(12) United States Patent
Kim et al.

(10) Patent No.: US 11,788,049 B2
(45) Date of Patent: Oct. 17, 2023

(54) CELL CULTURE SYSTEM

(71) Applicant: MICRO DIGITAL CO., LTD, Seongnam-si (KR)

(72) Inventors: Kyung Nam Kim, Gwangju-si (KR); Yong Bok Lee, Gimpo-si (KR); Chong Myung Kim, Seongnam-si (KR); Sun Young Kim, Seongnam-si (KR)

(73) Assignee: MICRO DIGITAL CO., LTD, Seongnam-si (KR)

( * ) Notice: Subject to any disclaimer, the term of this patent is extended or adjusted under 35 U.S.C. 154(b) by 0 days.

(21) Appl. No.: 17/854,303

(22) Filed: Jun. 30, 2022

(65) Prior Publication Data
US 2023/0151318 A1 May 18, 2023

(30) Foreign Application Priority Data
Nov. 18, 2021 (KR) .......................... 10-2021-0159740

(51) Int. Cl.
*C12M 3/06* (2006.01)
*C12M 1/00* (2006.01)
(Continued)

(52) U.S. Cl.
CPC ............ *C12M 27/16* (2013.01); *C12M 23/14* (2013.01); *C12M 23/48* (2013.01); *C12M 41/12* (2013.01); *C12M 41/42* (2013.01)

(58) Field of Classification Search
None
See application file for complete search history.

(56) References Cited

U.S. PATENT DOCUMENTS

| 5,057,429 A | 10/1991 | Watanabe et al. |
| 9,738,863 B2 | 8/2017 | Andersson et al. |

(Continued)

FOREIGN PATENT DOCUMENTS

| CN | 101586073 A | * 11/2009 | ............ C12M 21/04 |
| JP | H04-348783 A | 12/1992 | |

(Continued)

OTHER PUBLICATIONS

English Language Machine Translation of Suzuki et al. (JP 04348783), pp. 1-8 (May 5, 2023). (Year: 2023).*

(Continued)

*Primary Examiner* — William H. Beisner
(74) *Attorney, Agent, or Firm* — Bridgeway IP Law Group, PLLC; Sang Ho Lee; Hyun Woo Shin

(57) ABSTRACT

Provided is a cell culture system capable of mixing a medium for culturing animal or plant cells. The cell culture system includes a body, a movable plate including an accommodation space accommodating a culture bag accommodating a medium to mix the medium, and being tiltable in multiple directions by a central joint mounted at a first location of the body, a first actuator mounted between the body and a second location of the movable plate to move the movable plate, a second actuator mounted between the body and a third location of the movable plate to move the movable plate, and a controller for applying a control signal to the first and second actuators, wherein a first angle between a first reference line extending from the first location to the second location, and a second reference line extending from the first location to the third location is 120°.

13 Claims, 15 Drawing Sheets

(51) Int. Cl.
    *C12M 1/34*           (2006.01)
    *C12M 3/00*           (2006.01)

(56)                   References Cited

U.S. PATENT DOCUMENTS

| | | | |
|---|---|---|---|
| 10,590,374 | B2 | 3/2020 | Ho et al. |
| 2006/0013063 | A1* | 1/2006 | Singh ...................... B01F 31/23 |
| | | | 366/239 |
| 2017/0349870 | A1* | 12/2017 | Bjurman ................ C12M 41/00 |
| 2018/0002667 | A1 | 1/2018 | Keskar et al. |
| 2020/0401133 | A1* | 12/2020 | Armbrust ............. G05D 1/0061 |

FOREIGN PATENT DOCUMENTS

| | | | | |
|---|---|---|---|---|
| JP | 2012239401 A | * | 12/2012 | ............ C12M 23/24 |
| JP | 2018-019631 A | | 2/2018 | |
| JP | 2019-522979 A | | 8/2019 | |
| KR | 10-2014-0134436 A | | 11/2014 | |
| KR | 10-1784233 B1 | | 10/2017 | |

OTHER PUBLICATIONS

English Language Machine Translation of Kim (KR 101784233), pp. 1-11 (May 4, 2023). (Year: 2023).*

* cited by examiner

CELL CULTURE SYSTEM

CROSS-REFERENCE TO RELATED PATENT APPLICATION

This application claims the benefit of Korean Patent Application No. 10-2021-0159740, filed on Nov. 18, 2021, in the Korean Intellectual Property Office, the disclosure of which is incorporated herein in its entirety by reference.

BACKGROUND

1. Field

The present invention relates to a cell culture system and, more particularly, to a cell culture system capable of mixing and culturing cells in a medium for culturing animal or plant cells to produce raw materials for medications or vaccines, e.g., proteins.

2. Description of the Related Art

In general, the cell culture industry for culturing animal or plant cells may use various devices such as a medium mixing device for mixing a medium (or culture medium) appropriately for a culture environment, a cell culture device capable of culturing animal or plant cells in the medium, an isolation and purification device for isolating a desired material from the medium, and a genetic modification device.

Due to the current growth of the animal cell culture industry, a cell culture system for bioprocesses may use various devices for rotating and mixing a medium by using an impeller or a propeller.

However, the existing cell mixing method using the impeller or propeller may cause cell damage due to shear force based on direct contact between cells and the impeller or propeller, cause contamination because the impeller or propeller with a complicated shape may not be easily thoroughly cleaned, and require an additional cost to produce the impeller or propeller.

In an existing medium mixing device, which uses a motor provided with a rotating wheel for stirring to uniformly mix a medium accommodated in a disposable culture bag, the medium may not be mixed in various directions, and the rotating wheel needs to be increased in size or number or the motor needs to be increased in scale, size, capacity, or performance when the medium to be mixed is increased in volume, thereby greatly increasing costs to produce the device and products.

Furthermore, due to the inefficiency based on mechanical restrictions, e.g., the rotating wheel, the existing medium mixing device has poor performance in mixing the medium, wastes much energy, and thus may not increase product performance.

In addition, because the existing medium mixing device may only mix the medium, a user needs to mix the medium and then move the culture bag to a separate culture device to culture cells in a cell culture system.

SUMMARY

The present invention provides a cell culture system capable of increasing a degree of freedom and a degree of mixing of a medium by mixing the medium in multiple directions including forward, backward, leftward, rightward, upward, and downward directions, of achieving a semi-permanent lifespan based on very stable operation through a plurality of cycles by precisely positioning a first actuator, a second actuator, and an auxiliary joint at 120° with respect to a central joint, of greatly increasing device scale, performance, efficiency, and productivity by using a plurality of links, of greatly reducing a cost and a production time, and of culturing cells in the medium while mixing the medium. However, the scope of the present invention is not limited thereto.

According to an aspect of the present invention, there is provided a cell culture system including a body, a movable plate including an accommodation space accommodating a culture bag accommodating a medium to mix the medium, and being tiltable in multiple directions by a central joint mounted at a first location of the body, a first actuator mounted between the body and a second location of the movable plate to move the movable plate, a second actuator mounted between the body and a third location of the movable plate to move the movable plate, and a controller for applying a control signal to the first and second actuators, wherein a first angle between a first reference line extending from the first location to the second location, and a second reference line extending from the first location to the third location is 120°.

The cell culture system may further include an auxiliary joint mounted between the body and a fourth location of the movable plate to prevent vibration of the movable plate.

A second angle between the second reference line and a third reference line extending from the first location to the fourth location may be 120°, and a third angle between the third reference line and the first reference line may be 120°.

Each of the first and second actuators may include a motor mounted on the body, a first link rotated by the motor, and a second link having one end link-coupled to the first link, and another end link-coupled to the movable plate.

The central joint may include a universal joint.

The movable plate may include a box-shaped medium tank having an opening thereon and including the accommodation space therein, a cover for covering the opening of the medium tank, a temperature controller mounted on a bottom surface of the medium tank to control a temperature of the medium, and a tank frame mounted under the bottom surface of the medium tank to support the medium tank.

The movable plate may further include a culture bag presser for pressing the culture bag when the culture bag accommodated in the accommodation space inflates.

The culture bag presser may include a pressing frame consisting of horizontal and vertical bars.

The movable plate may further include a pressing actuator mounted in the cover to lift or lower the culture bag presser, and an inflation pressure gauge for measuring an inflation pressure applied to the pressing frame, and the controller may apply an up/down control signal to the pressing actuator based on an inflation pressure signal measured by the inflation pressure gauge.

The body may include a main frame for mounting the first actuator on a left side thereof, mounting the second actuator on a right side thereof, and mounting the central joint on a center thereof, a case for protecting the main frame, and caster wheels mounted under the main frame.

The body may further include a wheel frame mounted between the caster wheels and the main frame, and one or more load cells mounted between the main frame and the wheel frame, and the controller may apply a control signal to the first and second actuators based on a load signal received from the load cells.

The case may include a link hole, through which a second link sufficiently passes, in a top surface thereof to accommodate at least a part of a first or second link.

The controller may select and apply at least one of a first actuator up-second actuator up control signal, a first actuator up-second actuator down control signal, a first actuator down-second actuator up control signal, and a first actuator down-second actuator down control signal to the first and second actuators to successively tilt the movable plate in forward, backward, leftward, and rightward directions.

The controller may apply a pause control signal to pause operation for a certain time and then restart the operation, while successively tilting the movable plate in forward, backward, leftward, and rightward directions.

The controller may apply a return control signal to return to a paused or horizontal state, when operation is restarted after being paused while successively tilting the movable plate in forward, backward, leftward, and rightward directions.

The controller may pre-store a reference load signal generated by the load cells, determine normal or abnormal operation by comparing the reference load signal to a real-time load signal of the load cells, and output an operation stop signal, a normal state follow signal, a feedback signal, or a warning signal when the abnormal operation is determined.

The movable plate may be tilted backward when both of the second and third locations are lifted by lifting both of the first and second actuators, or tilted forward when both of the second and third locations are lowered by lowering both of the first and second actuators.

The movable plate may be tilted rightward when the second location is lifted and the third location is lowered by lifting the first actuator and lowering the second actuator, or tilted leftward when the second location is lowered and the third location is lifted by lowering the first actuator and lifting the second actuator.

According to another aspect of the present invention, there is provided a cell culture system including a body, a movable plate including an accommodation space accommodating a culture bag accommodating a medium to mix the medium, and being tiltable in multiple directions by a central joint mounted at a first location of the body, a first actuator mounted between the body and a second location of the movable plate to move the movable plate, a second actuator mounted between the body and a third location of the movable plate to move the movable plate, and a controller for applying a control signal to the first and second actuators, wherein a first reference line extending from the first location to the second location, a second reference line extending from the first location to the third location, and a third reference line extending from the first location to a fourth location are set, and an angle between the third reference line and the first reference line is the same as an angle between the third reference line and the second reference line.

According to another aspect of the present invention, there is provided a cell culture system including a body, a movable plate including an accommodation space accommodating a culture bag accommodating a medium to mix the medium, and being tiltable in multiple directions by a central joint mounted at a first location of the body, a first actuator mounted between the body and a second location of the movable plate to move the movable plate, a second actuator mounted between the body and a third location of the movable plate to move the movable plate, and a controller for applying a control signal to the first and second actuators, wherein the movable plate further includes a culture bag presser for pressing the culture bag when the culture bag accommodated in the accommodation space inflates.

BRIEF DESCRIPTION OF THE DRAWINGS

The above and other features and advantages of the present invention will become more apparent by describing in detail embodiments thereof with reference to the attached drawings in which.

DETAILED DESCRIPTION

Figure 1:
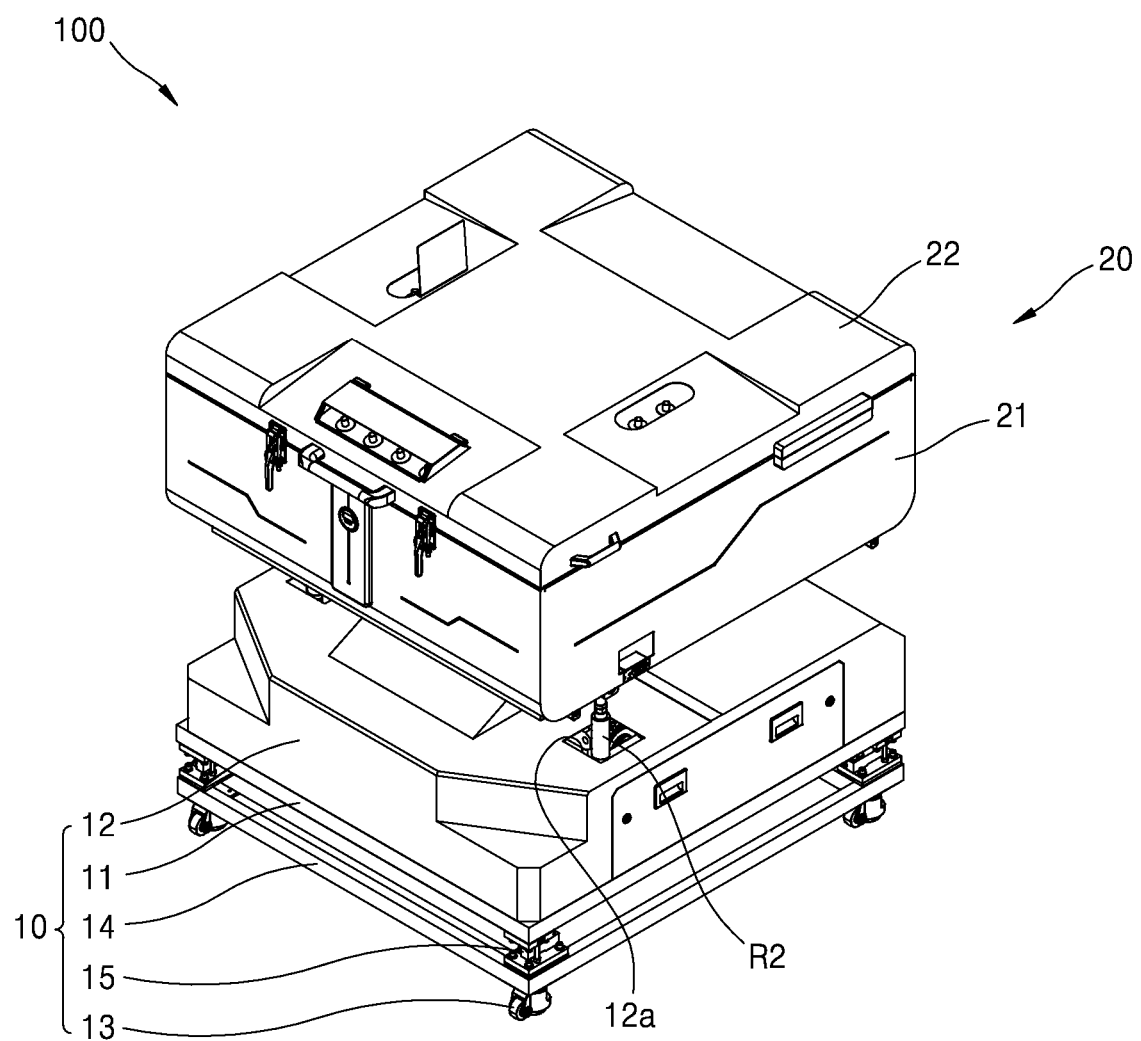
FIG. 1 is an exterior perspective view conceptually illustrating a cell culture system according to some embodiments of the present invention.

Hereinafter, the present invention will be described in detail by explaining embodiments of the invention with reference to the attached drawings.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the thicknesses or sizes of layers are exaggerated for clarity or convenience of explanation.

It will be understood that when an element, such as a layer, a region, or a substrate, is referred to as being "on", "connected to", "stacked on", or "coupled to" another element, it may be directly on, connected to, stacked on, or coupled to the other element or intervening elements may be present. In contrast, when an element is referred to as being "directly on", "directly connected to", "directly stacked on", or "directly coupled to" another element or layer, there are no intervening elements or layers present. Like reference numerals denote like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Spatially relative terms, such as "above", "upper", "beneath", "below", "lower", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "above" may encompass both an orientation of above and below. The device may be otherwise oriented (rotated 90 degrees or at other orientations) and the spatially relative descriptors used herein interpreted accordingly.

The terminology used herein is for the purpose of describing particular embodiments and is not intended to limit the invention. As used herein, the singular forms "a", "an", and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, the embodiments of the invention should not be construed as limited to the particular shapes of regions illustrated herein, but are to include deviations in shapes that result, for example, from manufacturing.

Figure 2:
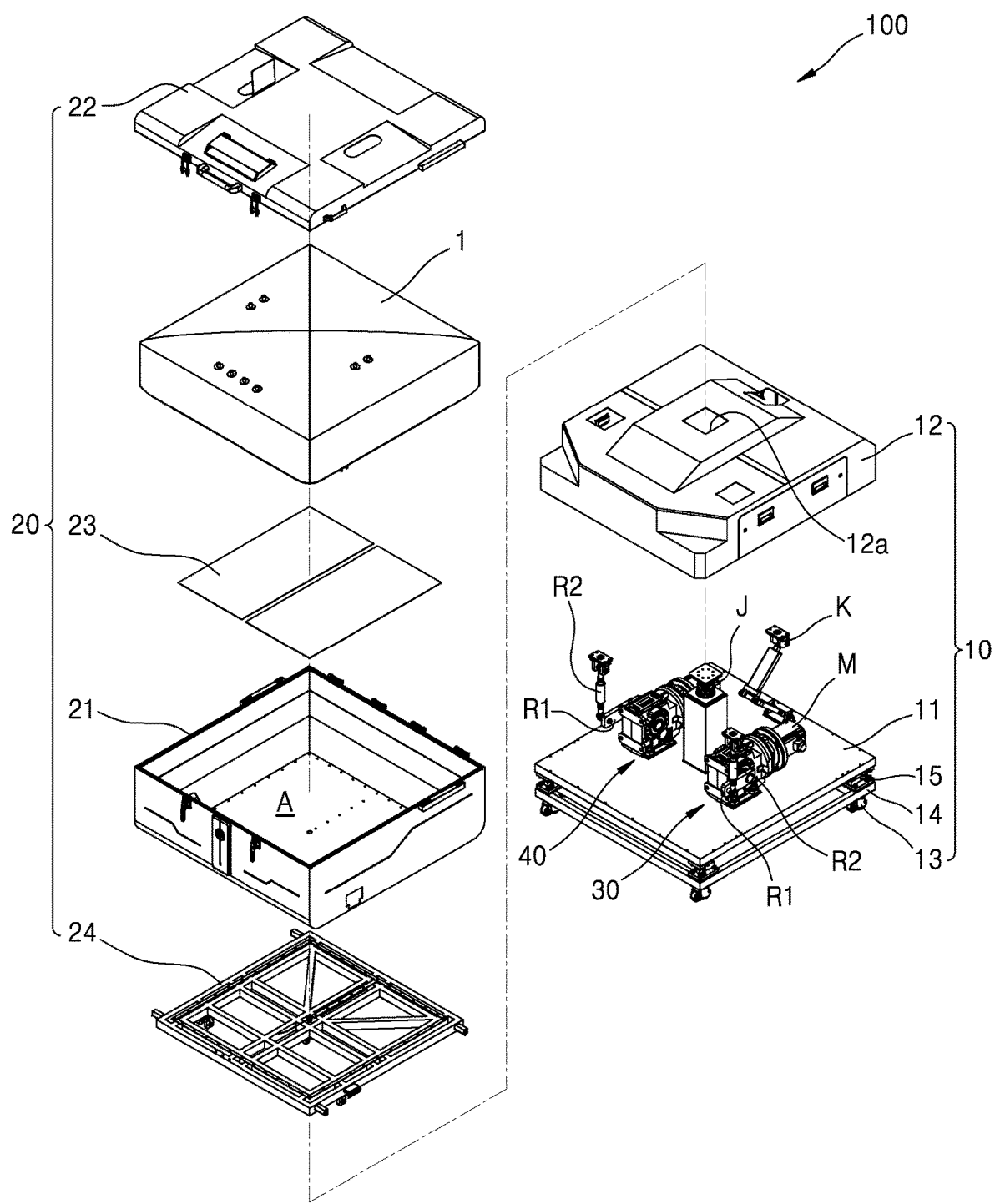
FIG. 2 is an exploded perspective view of the cell culture system of FIG. 1.
Figure 3:
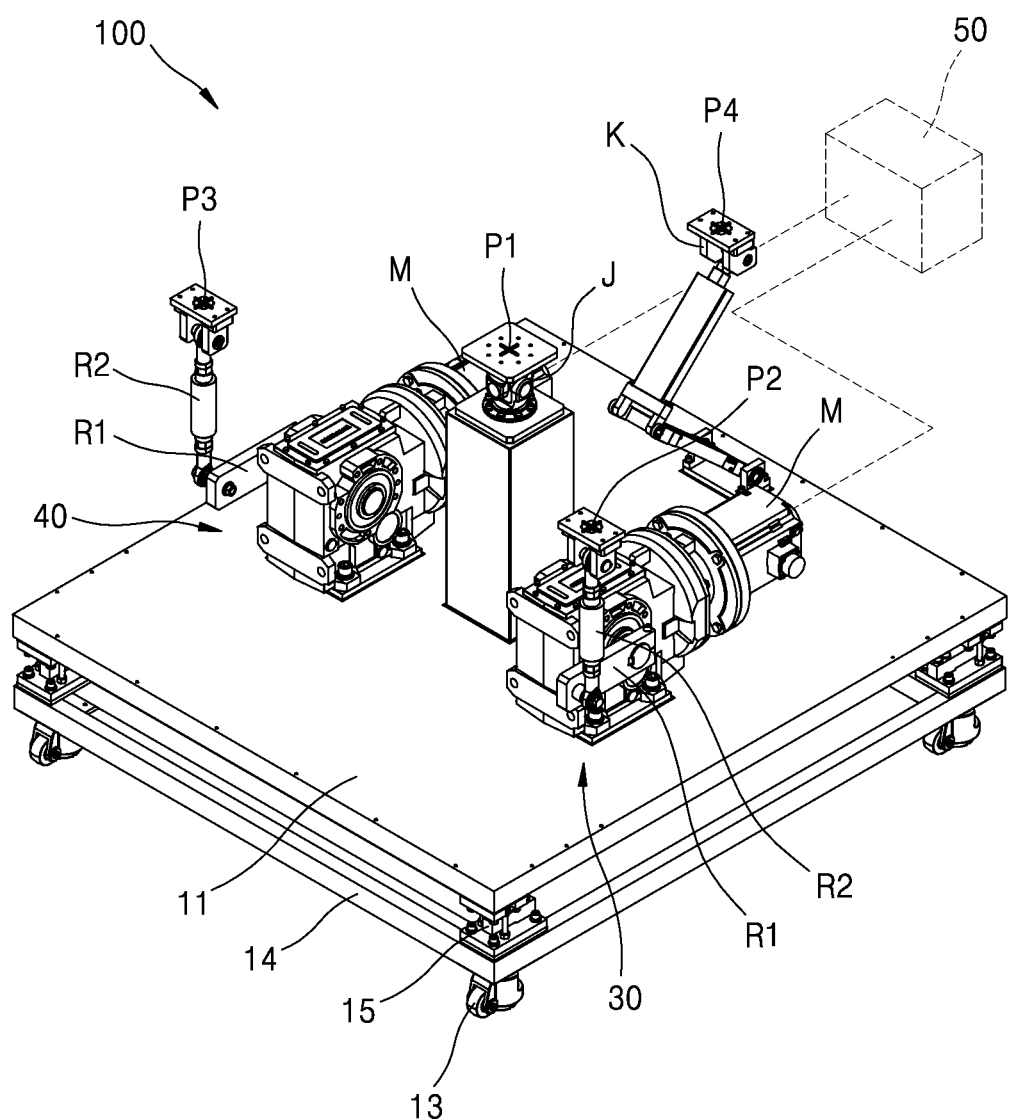
FIG. 3 is a perspective view of a central joint, a first actuator, a second actuator, and an auxiliary joint of the cell culture system of FIG. 2.
Figure 4:
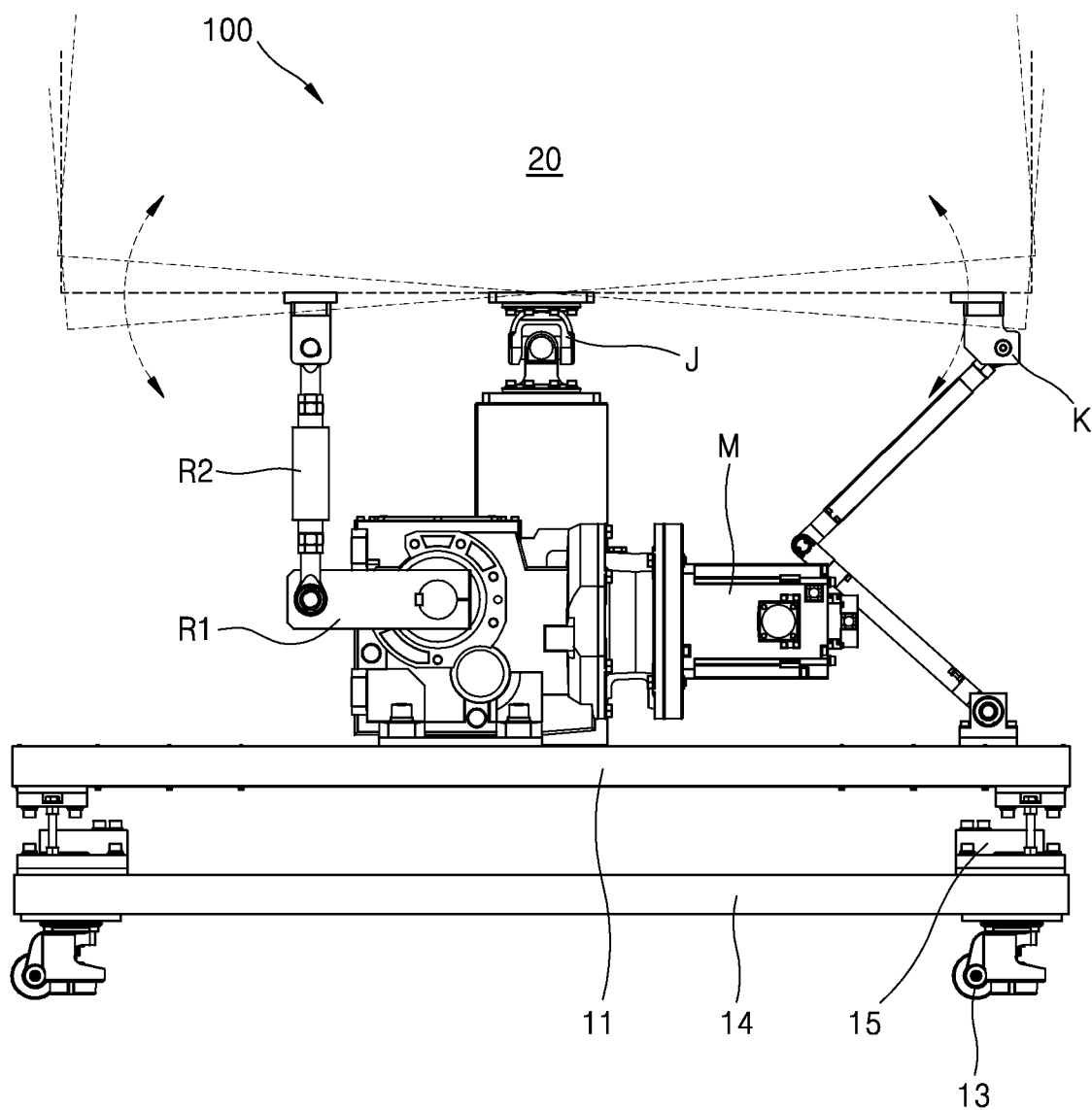
FIG. 4 is a side view showing an operation state of the cell culture system of FIG. 3.
Figure 5:
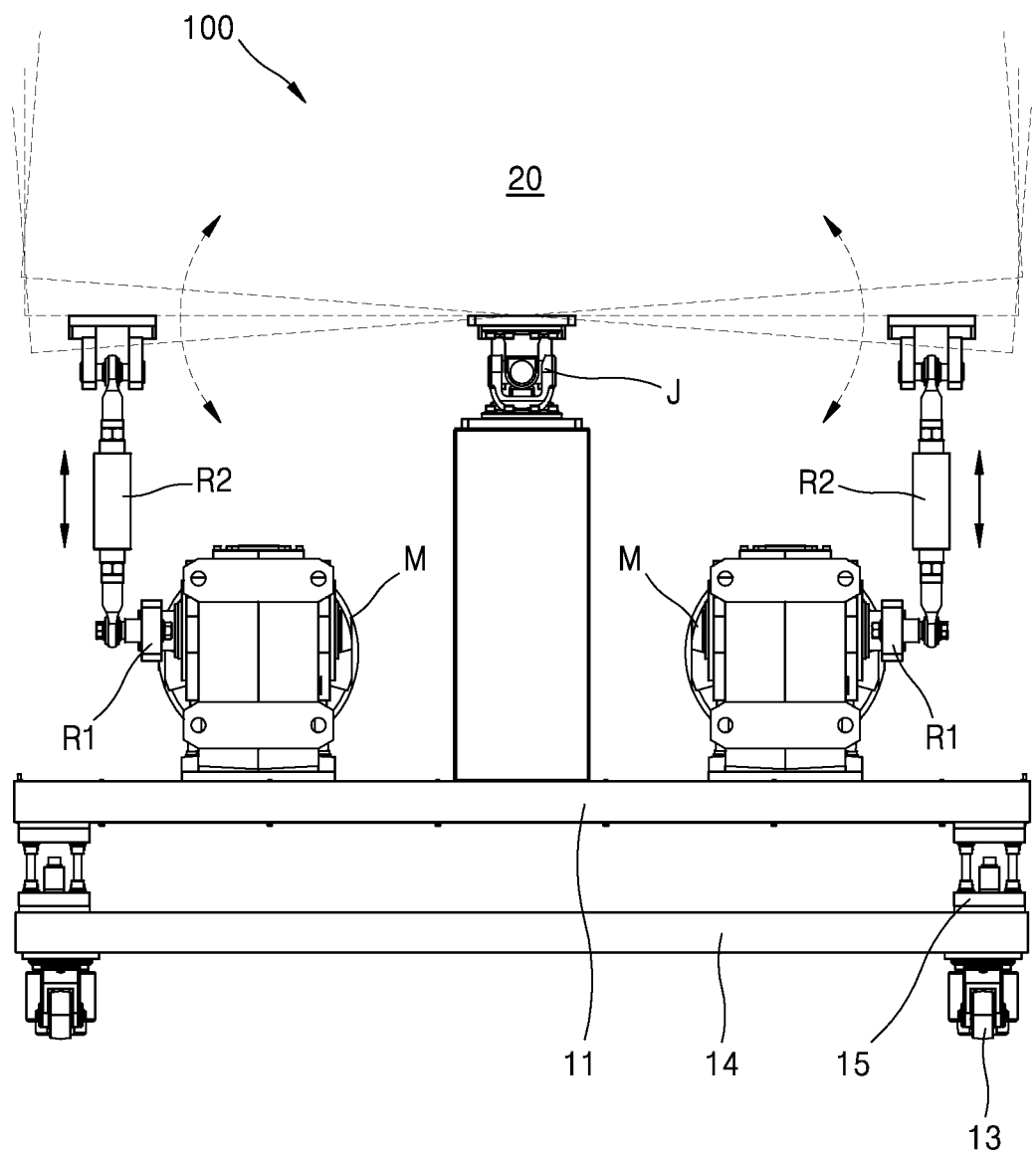
FIG. 5 is a front view showing an operation state of the cell culture system of FIG. 3.
Figure 6:
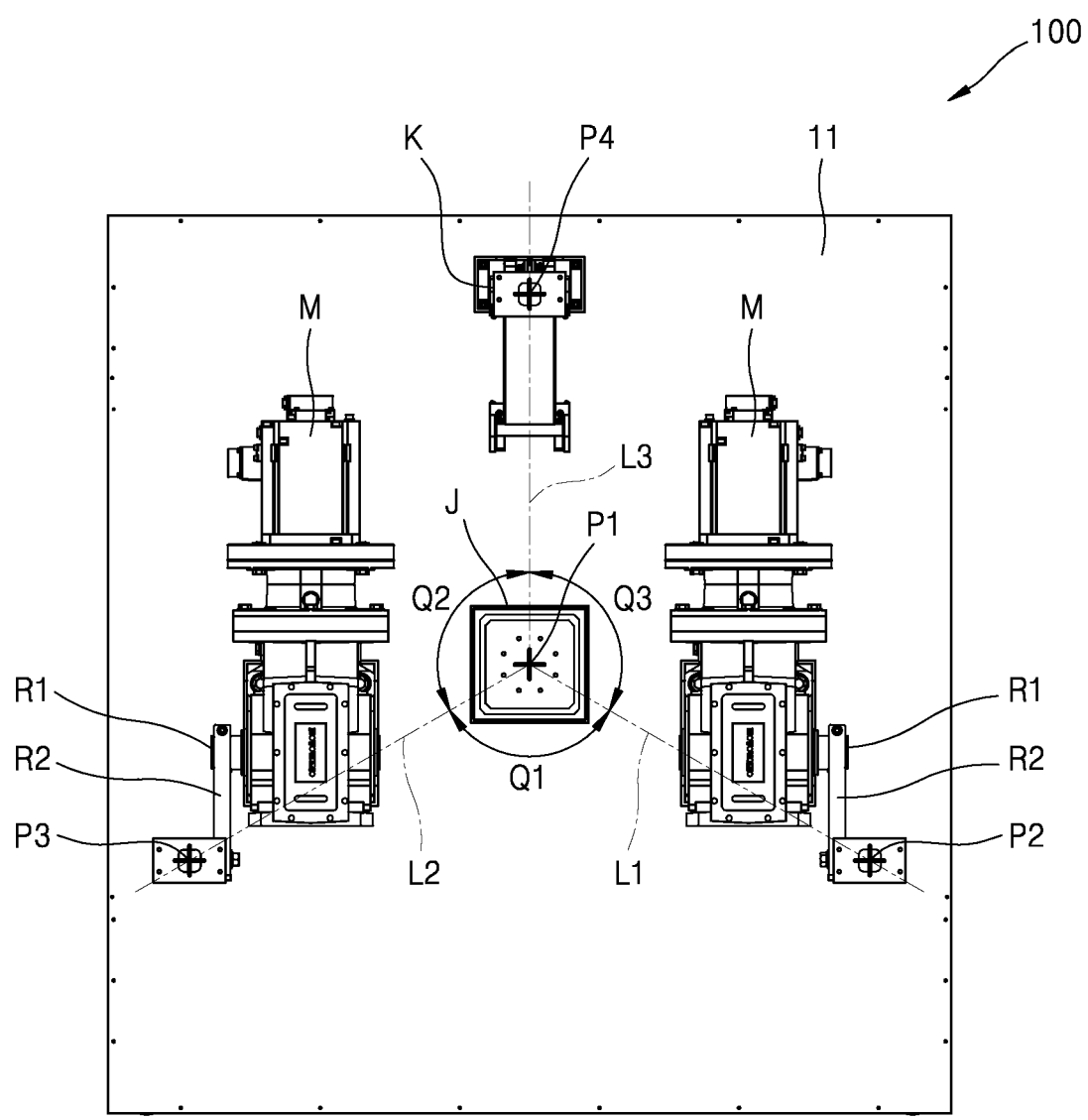
FIG. 6 is a plan view of the cell culture system of FIG. 3.

FIG. 1 is an exterior perspective view conceptually illustrating a cell culture system 100 according to some embodiments of the present invention, FIG. 2 is an exploded perspective view of the cell culture system 100 of FIG. 1, FIG. 3 is a perspective view of a central joint J, a first actuator 30, a second actuator 40, and an auxiliary joint K of the cell culture system 100 of FIG. 2, FIG. 4 is a side view showing an operation state of the cell culture system 100 of FIG. 3, FIG. 5 is a front view showing an operation state of the cell culture system 100 of FIG. 3, and FIG. 6 is a plan view of the cell culture system 100 of FIG. 3.

As illustrated in FIGS. 1 to 6, the cell culture system 100 according to some embodiments of the present invention may mainly include a body 10, a movable plate 20, the first actuator 30, the second actuator 40, and a controller 50.

For example, as illustrated in FIG. 3, the body 10 may have sufficient durability and strength to support the movable plate 20 and the first and second actuators 30 and 40 mentioned above, and include various types of vertical members, horizontal members, panels, etc.

Specifically, for example, as illustrated in FIGS. 1 and 3, the body 10 may include a main frame 11 for mounting the first actuator 30 on a left side thereof, mounting the second actuator 40 on a right side thereof, and mounting the central joint J on a center thereof, a case 12 for protecting the main frame 11, and caster wheels 13 mounted under the main frame 11.

For example, the body 10 may further include a wheel frame 14 mounted between the caster wheels 13 and the main frame 11, and one or more load cells 15 mounted between the main frame 11 and the wheel frame 14, e.g., four load cells 15 corresponding to four caster wheels 13.

Therefore, the controller 50 may apply a control signal to the first and second actuators 30 and 40 based on a load signal received from the load cells 15.

For example, the controller 50 may pre-store a reference load signal generated by the load cells 15 when hydrodynamic flow characteristics of media (or culture media) accommodated in culture bags 1 are normal, based on an operation state, an operation position, an operation voltage, an operation current, an operation load, or the like of the first or second actuator 30 and 40, determine normal or abnormal operation by comparing the reference load signal to a real-time load signal of the load cells 15, and take a follow-up action, for example, output an operation stop signal, a normal state follow signal, a feedback signal, or a warning signal, when the abnormal operation is determined.

Accordingly, using the load cells 15, it may be determined in real time whether the culture bags 1 with a large volume are normally mixed, and safety accidents that occur due to various component failures or malfunctions may be prevented in advance.

For example, to increase device safety by preventing exposure of links R1 and R2 as much as possible, the case 12 may include a link hole 12a, through which a second link R2 sufficiently passes, in a top surface thereof to accommodate at least a part of a first or second link R1 or R2 to be described below.

However, the main frame 11, and the case 12, the caster wheels 13, the wheel frame 14, and the load cells 15 are not limited to the illustrated shapes or types and may have various shapes and types.

Therefore, a user may easily transport the body 10 to a desired place by using the caster wheels 13, and the movable plate 20 and the first and second actuators 30 and 40 may be firmly supported.

For example, as illustrated in FIG. 2, the movable plate 20 may be a box-shaped structure which includes an accommodation space A capable of accommodating a medium or the culture bag 1 accommodating the medium to mix the medium, and is tiltable in multiple directions by the central joint J mounted at a first location P1 of the body 10.

Herein, the central joint J may include a universal joint capable of freely rotating about multiple axes. However, the central joint J may also use various other types of joints, e.g., a ball joint.

Specifically, for example, as illustrated in FIG. 2, the movable plate 20 may include a box-shaped medium tank 21 having an opening thereon and including the accommodation space A therein, a cover 22 for covering the opening of the medium tank 21, a temperature controller 23 mounted on a bottom surface of the medium tank 21 to control a temperature of the medium, and a tank frame 24 mounted under the bottom surface of the medium tank 21 to support the medium tank 21.

Herein, the temperature controller 23 is a device capable of heating or cooling the medium tank 21, and may use not only a heater or a thermoelectric element using electric resistance heat, but also various cooling devices such as a water-cooled heat exchanger capable of circulating a refrigerant, or an air-cooled heat exchanger capable of using natural convection or a blowing fan.

Therefore, the user may keep warm by closing the cover 22 while the medium or the culture bag 1 is accommodated in the medium tank 21, and maintain the medium at an optimal culture temperature by using the temperature controller 23.

Meanwhile, although not shown in the drawings, for more accurate cultivation, at least one of a weight sensor for measuring a weight of the medium, a temperature sensor for measuring a temperature of the medium, an oxygen sensor for measuring an oxygen concentration in the medium, an oxygen supplier for supplying oxygen to the medium, a pH sensor for measuring an acidity of the medium, an acid-base supplier for supplying an acidic or basic substance to the medium, a nutrient concentration sensor for measuring a nutrient concentration in the medium, a nutrient supplier for supplying nutrients to the medium, and combinations thereof may be selected and mounted in the medium tank 21.

For example, as illustrated in FIGS. 3 to 6, the first actuator 30 is a device mounted between the body 10 and a second location P2 of the movable plate 20 to move the movable plate 20, and may be provided with various types of power sources such as a motor or a cylinder, and various types of power transmitters capable of receiving power from the power source and converting the power into vertical or rotational motion.

Specifically, for example, as illustrated in FIGS. 3 to 6, the first actuator 30 may include a motor M mounted on the body 10, a first link R1 rotated by the motor M, and a second link R2 having one end link-coupled to the first link R1, and another end link-coupled to the movable plate 20.

Herein, the motor M may include various servo motors, step motors, or gear boxes capable of angularly rotating the first link R1.

The first and second links R1 and R2 are rod-shaped links which are hinge-coupled to each other, and may be provided with a multiaxial joint or loosely to smoothly tilt the movable plate 20 in multiaxial directions.

Therefore, when the motor M rotates the first link R1 at a first link angle, the one end of the second link R2 may move along a rotation path of the first link R1 and the other end thereof may lift or lower the second location P2 of the movable plate 20.

For example, as illustrated in FIGS. 3 to 5, the second actuator 40 is a device mounted between the body 10 and a third location P3 of the movable plate 20 to move the movable plate 20, and may be provided with various types of power sources such as a motor or a cylinder, and various types of power transmitters capable of receiving power from the power source and converting the power into vertical or rotational motion.

Specifically, for example, as illustrated in FIGS. 3 to 5, the second actuator 40 may also include a motor M mounted on the body 10, a first link R1 rotated by the motor M, and a second link R2 having one end link-coupled to the first link R1, and another end link-coupled to the movable plate 20.

Herein, the motor M and the first and second links R1 and R2 have the same configurations and functions as those of the first actuator 30, and a detailed description thereof is not provided herein.

Therefore, when the motor M rotates the first link R1 at a first link angle, one end of the second link R2 may move along a rotation path of the first link R1 and another end thereof may lift or lower the third location P3 of the movable plate 20.

Herein, as illustrated in FIG. 6, a first angle Q1 between a first reference line L1 extending from the first location P1 to the second location P2, and a second reference line L2 extending from the first location P1 to the third location P3 may be exactly 120°.

For example, the cell culture system 100 according to some embodiments of the present invention may further include the auxiliary joint K mounted between the body 10 and a fourth location P4 of the movable plate 20 to prevent vibration of the movable plate 20.

Herein, a second angle Q2 between the second reference line L2 and a third reference line L3 extending from the first location P1 to the fourth location P4 may also be exactly 120°, and a third angle Q3 between the third reference line L3 and the first reference line L1 may also be exactly 120°.

That is, because a total angle of one cycle corresponding to a sum of the first, second, and third angles Q1, Q2, and Q3 may be exactly 360° and thus a plurality of subsequent cycles may start at the same point, no strain may be caused on components based on very stable operation and a semi-permanent lifespan may be achieved.

However, 120° is merely an example of the first, second, and third angles Q1, Q2, and Q3, and the scope of the present invention is not limited thereto.

For example, the first, second, and third angles Q1, Q2, and Q3 may have a difference of about 1°, e.g., a range of 119° to 121°, in consideration of manufacturing tolerances.

Furthermore, for example, the first reference line L1 extending from the first location P1 to the second location P2, the second reference line L2 extending from the first location P1 to the third location P3, and the third reference line L3 extending from the first location P1 to the fourth location P4 may be set, and the third angle Q3 between the third reference line L3 and the first reference line L1 may be the same as the second angle Q2 between the third reference line L3 and the second reference line L2. The same angle may have a range greater than 0° and less than 180°.

Accordingly, as illustrated in FIG. 4, the movable plate 20 may be tilted backward when both of the second and third locations P2 and P3 are lifted by lifting both of the first and second actuators 30 and 40, or tilted forward when both of the second and third locations P2 and P3 are lowered by lowering both of the first and second actuators 30 and 40.

As illustrated in FIG. 5, the movable plate 20 may be tilted rightward when the second location P2 is lifted and the third location P3 is lowered by lifting the first actuator 30 and lowering the second actuator 40, or tilted leftward when the second location P2 is lowered and the third location P3 is lifted by lowering the first actuator 30 and lifting the second actuator 40.

To this end, the controller 50 configured to apply a control signal to the first and second actuators 30 and 40 may select and apply at least one of a first actuator up-second actuator up control signal, a first actuator up-second actuator down control signal, a first actuator down-second actuator up control signal, and a first actuator down-second actuator down control signal to the first and second actuators 30 and 40 to successively tilt the movable plate 20 in forward, backward, leftward, and rightward directions by using a certain program or a command input device.

Herein, the controller 50 may be provided inside or outside the body 10, and include a separate printed circuit board (PCB) control board or a microprocessor, or be configured using a personal computer or a server computer.

For example, in order to temporarily stabilize the media after being mixed, the controller 50 may apply a pause control signal to pause operation for a certain time and then restart the operation, while successively tilting the movable plate 20 in forward, backward, leftward, and rightward directions.

For example, in order to increase convenience of use in on/off operation, the controller 50 may apply a return control signal to return to a paused or horizontal state, when operation is restarted after being paused while successively tilting the movable plate 20 in forward, backward, leftward, and rightward directions. In addition, the controller 50 may be programmed to perform various operations based on user input.

Accordingly, damage to cells included in the medium may be greatly reduced because no impeller or propeller is used, contamination of the medium due to the impeller or propeller may be prevented, a production cost of equipment may be greatly reduced, a degree of freedom and a degree of mixing of the medium may be increased because the medium may be mixed in multiple directions including forward, backward, leftward, rightward, upward, and downward directions, a semi-permanent lifespan may be achieved, device scale, performance, efficiency, and productivity may be greatly increased by using a plurality of links, a cost and a production time may be greatly reduced, and cells in the medium may be cultured while mixing the medium.

Figure 7:
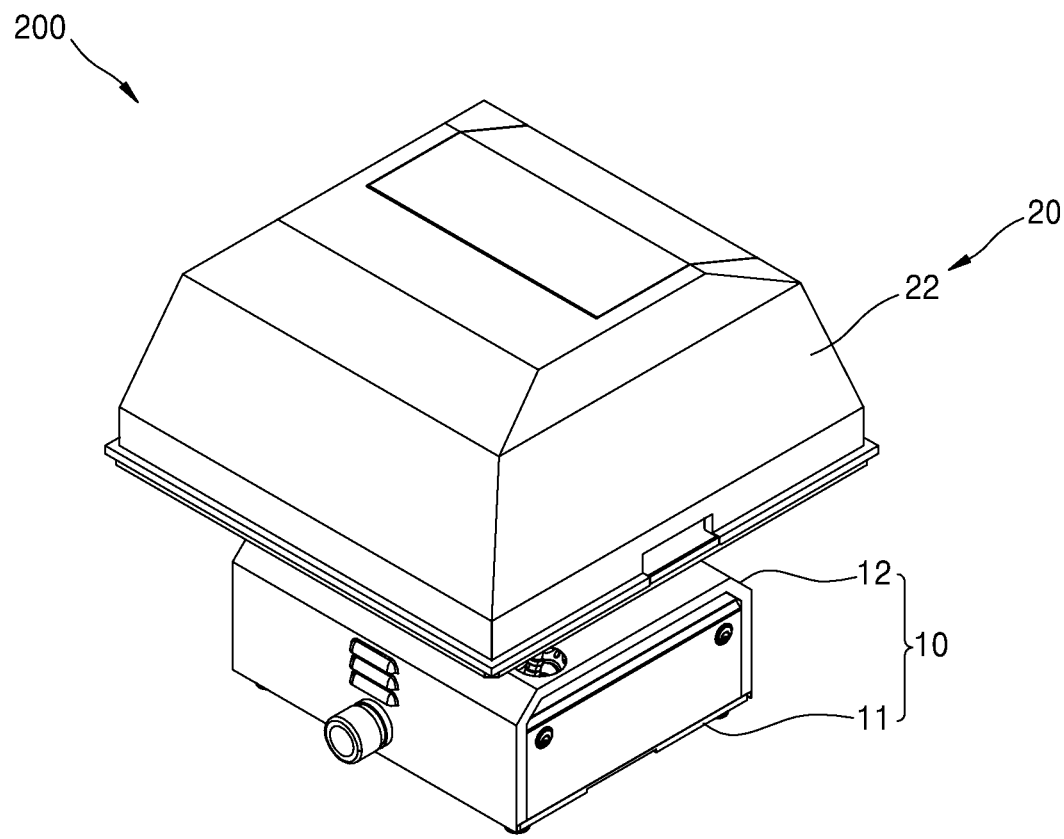
FIG. 7 is an exterior perspective view conceptually illustrating a cell culture system according to other embodiments of the present invention.
Figure 8:
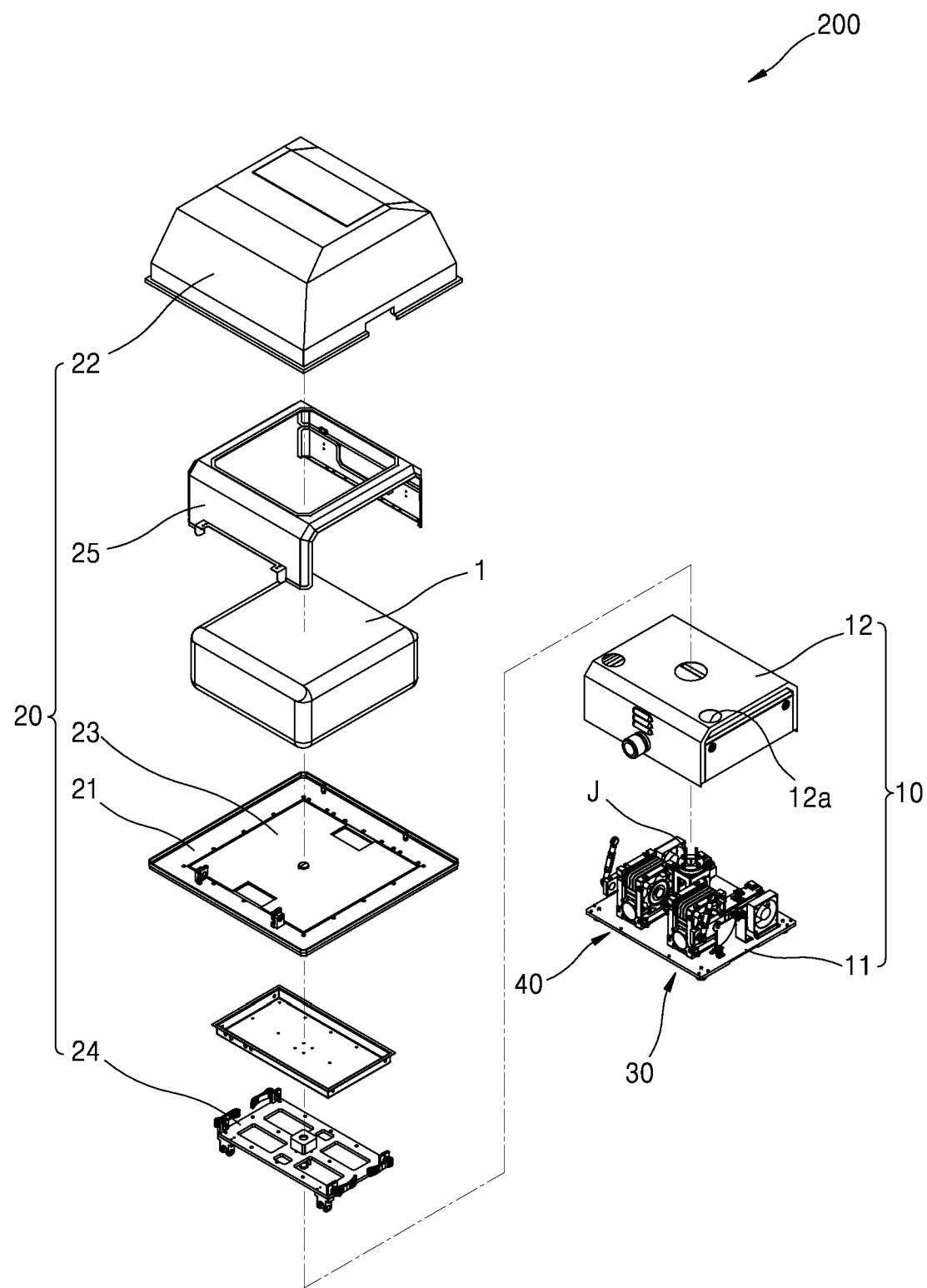
FIG. 8 is an exploded perspective view of the cell culture system of FIG. 7.

FIG. 7 is an exterior perspective view conceptually illustrating a cell culture system 200 according to other embodiments of the present invention, and FIG. 8 is an exploded perspective view of the cell culture system 200 of FIG. 7.

As illustrated in FIGS. 7 and 8, the cell culture system 200 according to other embodiments of the present invention may be implemented without the auxiliary joint K, the caster wheels 13, the wheel frame 14, or the load cells 15 described above in relation to FIGS. 1 to 6.

Figure 9:
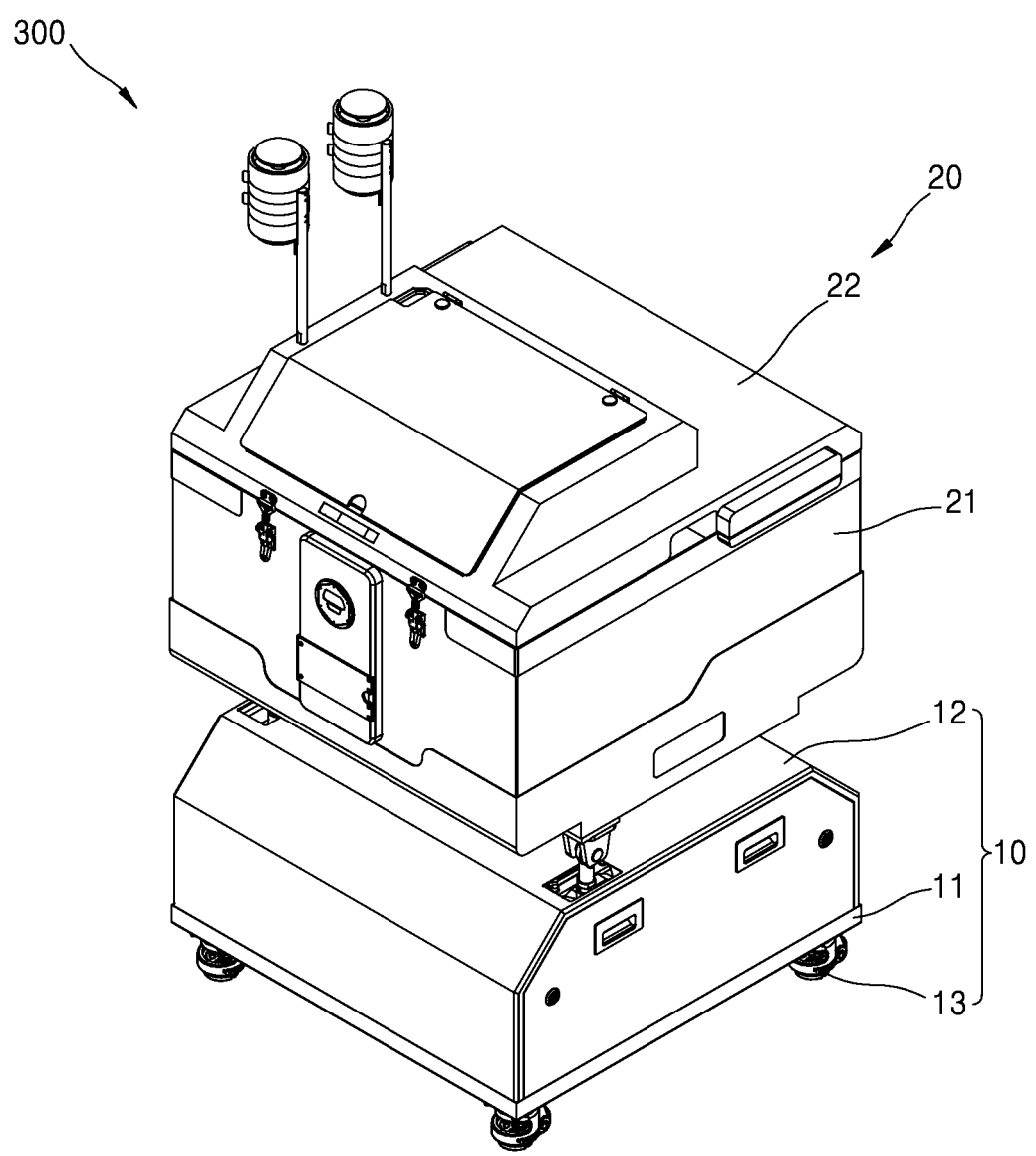
FIG. 9 is an exterior perspective view conceptually illustrating a cell culture system according to still other embodiments of the present invention.
Figure 10:
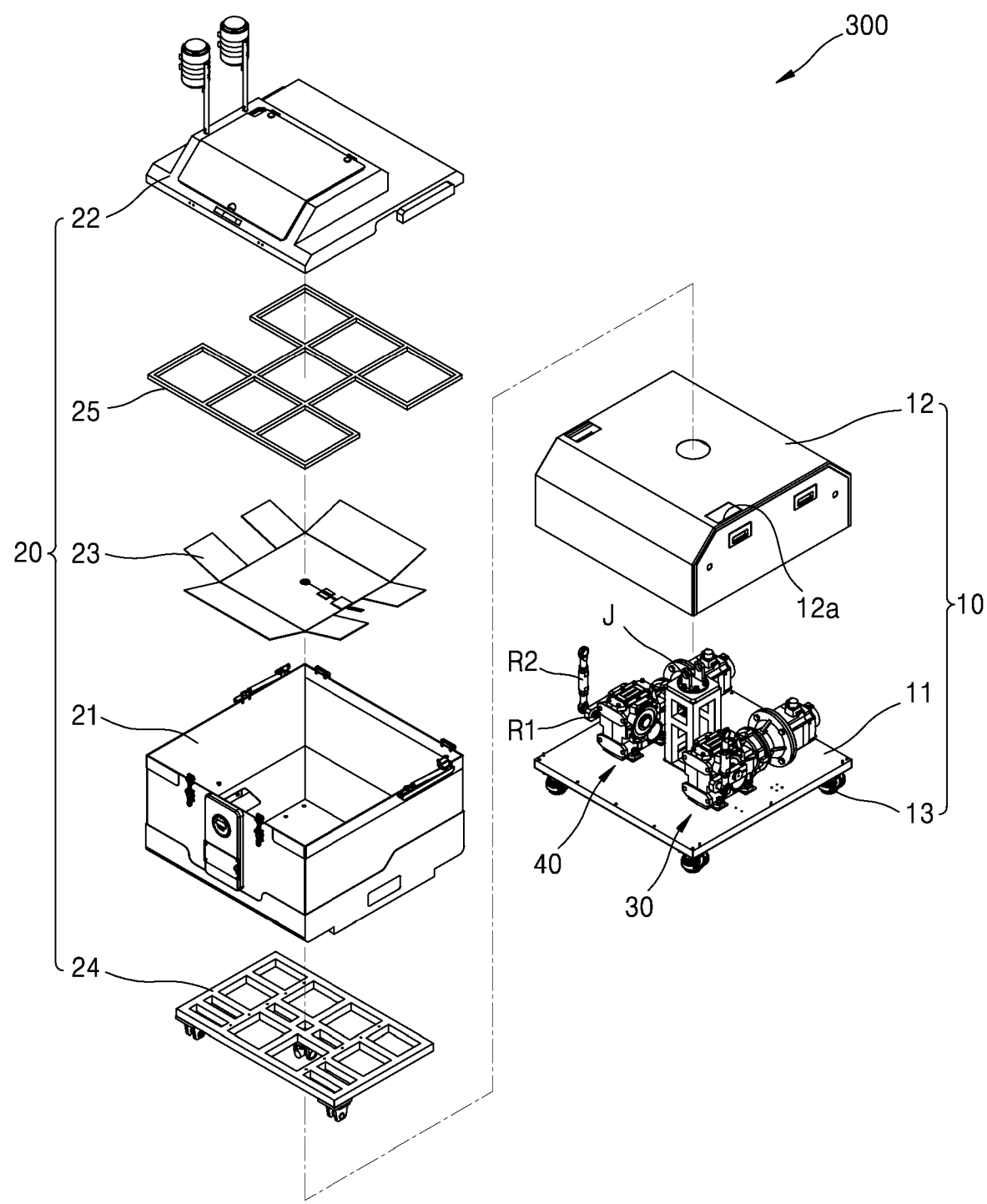
FIG. 10 is an exploded perspective view of the cell culture system of FIG. 9.

FIG. 9 is an exterior perspective view conceptually illustrating a cell culture system 300 according to still other embodiments of the present invention, and FIG. 10 is an exploded perspective view of the cell culture system 300 of FIG. 9.

As illustrated in FIGS. 9 and 10, the cell culture system 300 according to still other embodiments of the present invention may be implemented without the auxiliary joint K, the wheel frame 14, or the load cells 15 described above in relation to FIGS. 1 to 6.

Figure 11:
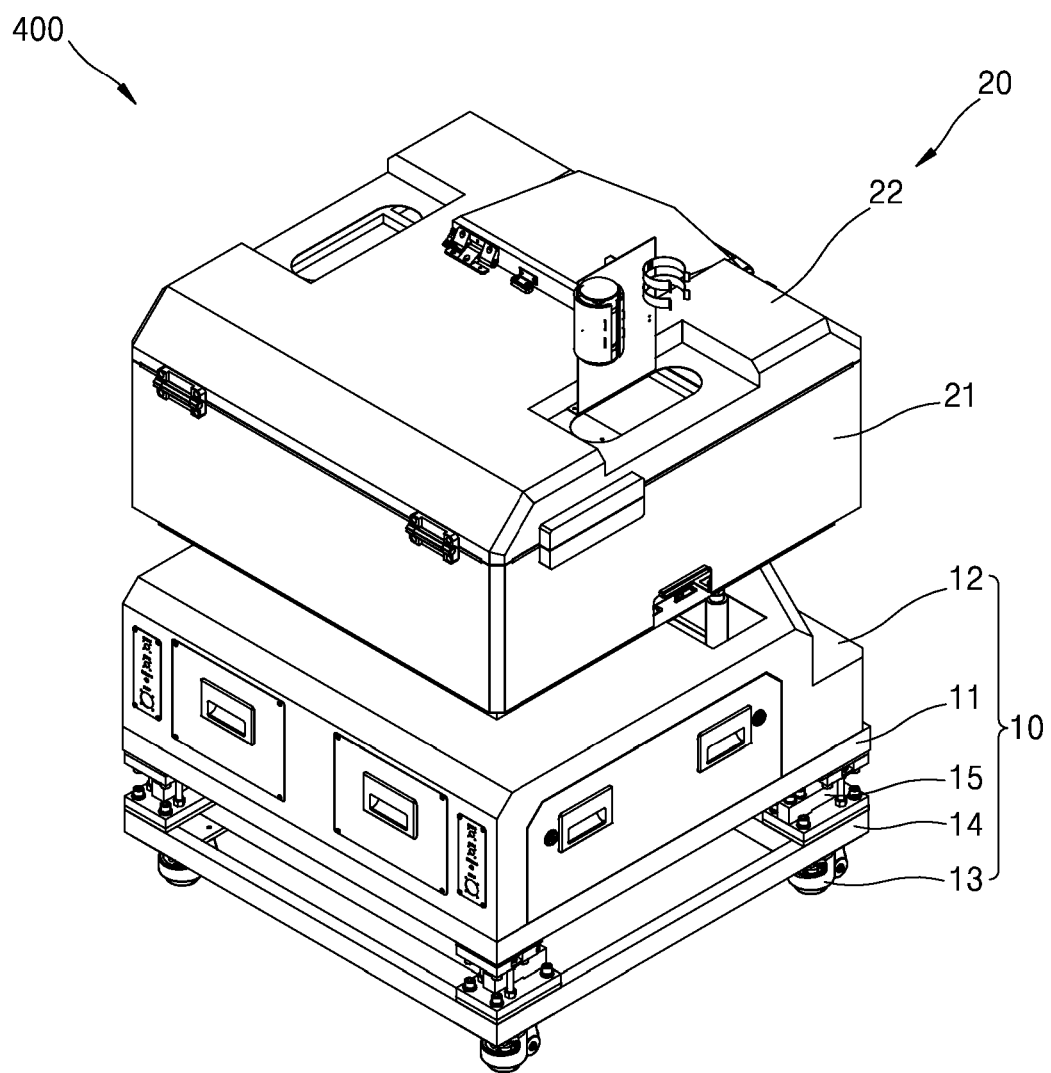
FIG. 11 is an exterior perspective view conceptually illustrating a cell culture system according to still other embodiments of the present invention.
Figure 12:
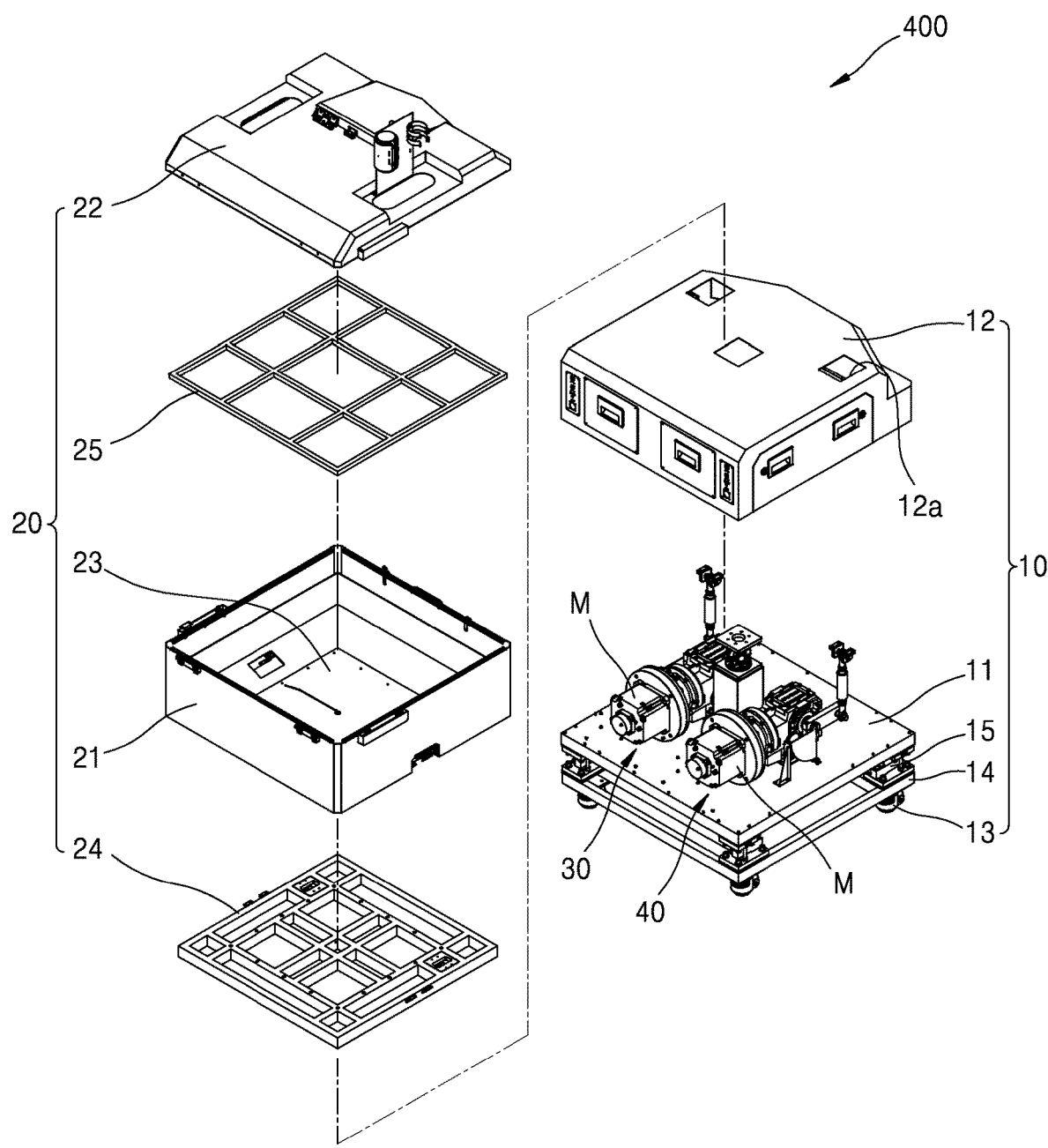
FIG. 12 is an exploded perspective view of the cell culture system of FIG. 11.

FIG. 11 is an exterior perspective view conceptually illustrating a cell culture system 400 according to still other embodiments of the present invention, and FIG. 12 is an exploded perspective view of the cell culture system 400 of FIG. 11.

As illustrated in FIGS. 11 and 12, the cell culture system 400 according to still other embodiments of the present invention may be implemented without the auxiliary joint K described above in relation to FIGS. 1 to 6.

Figure 13:
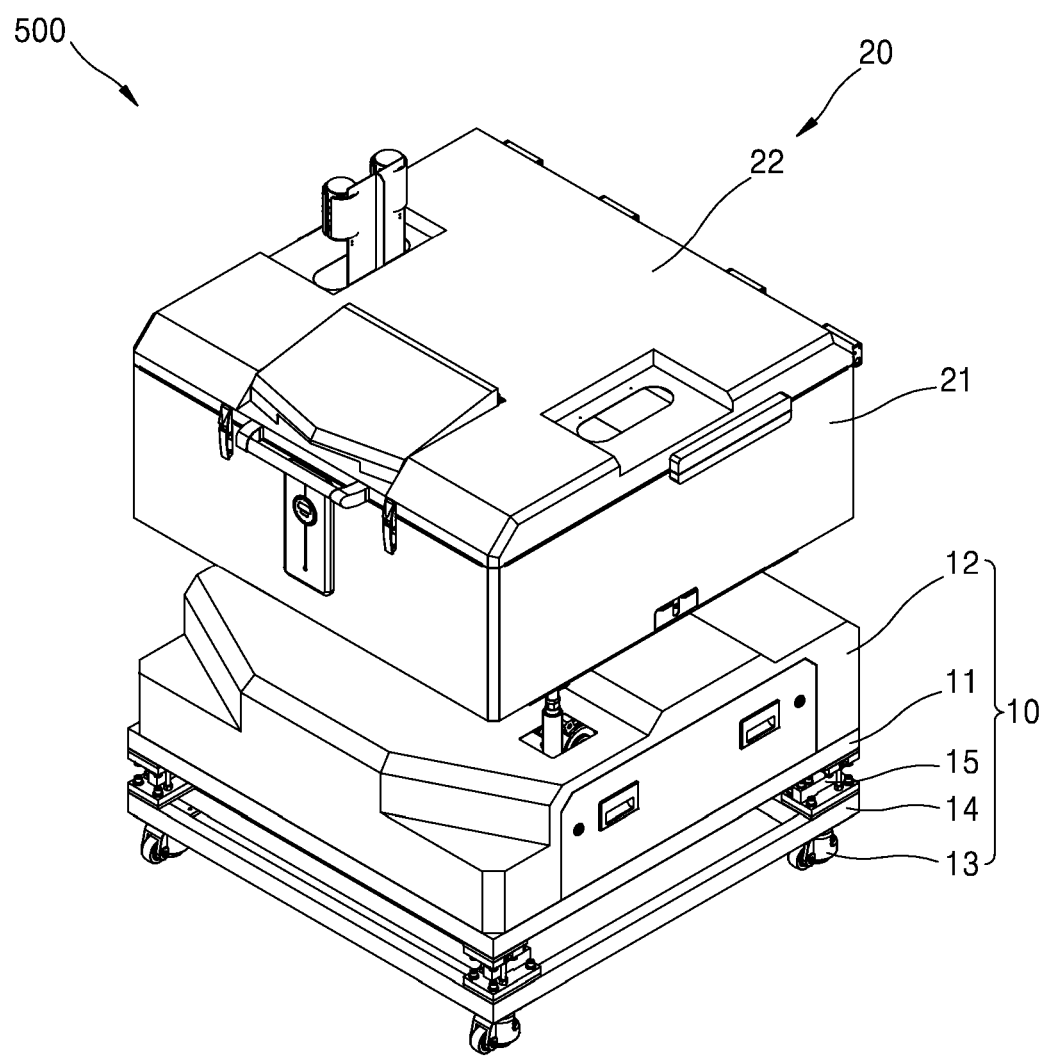
FIG. 13 is an exterior perspective view conceptually illustrating a cell culture system according to still other embodiments of the present invention.
Figure 14:
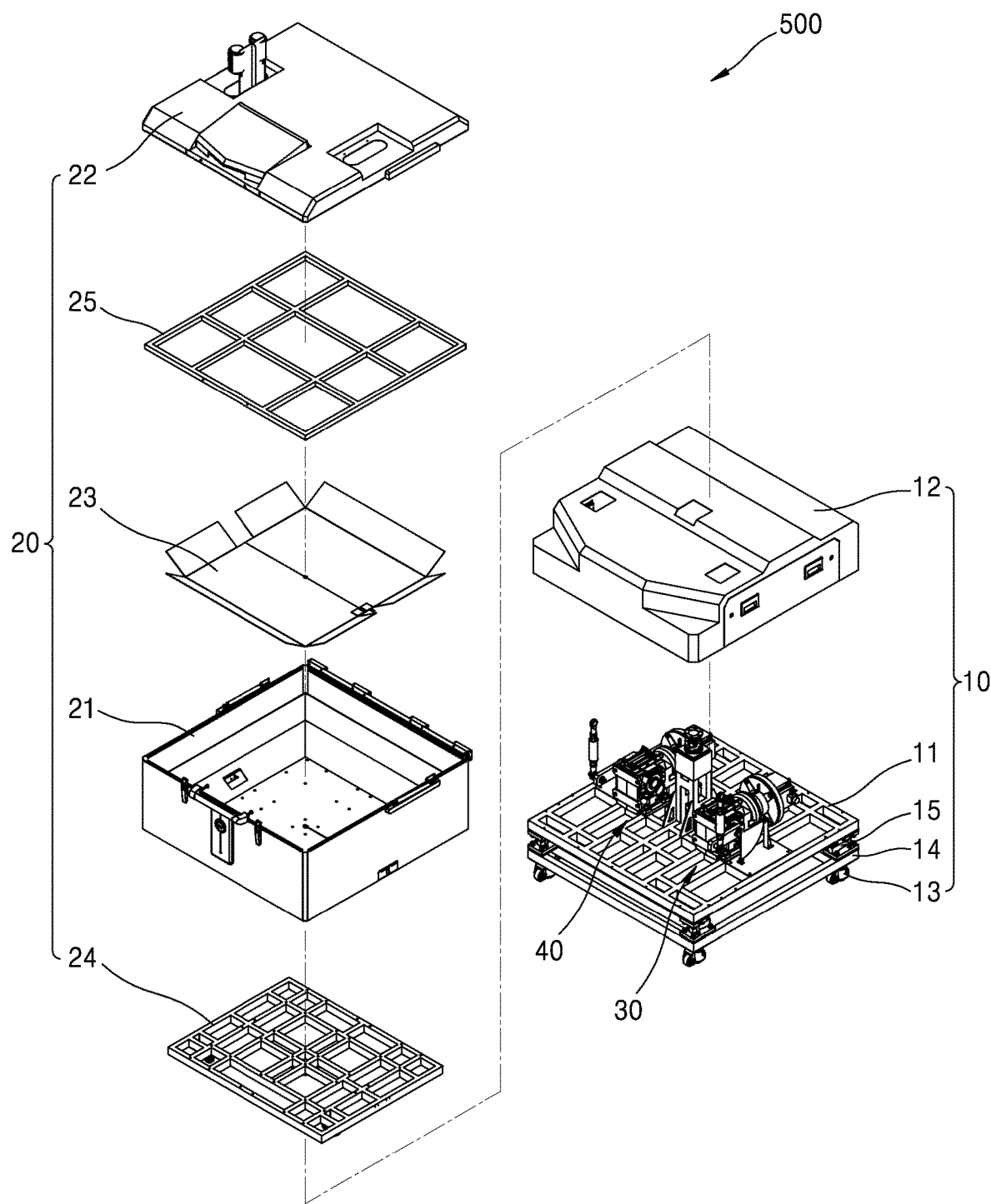
FIG. 14 is an exploded perspective view of the cell culture system of FIG. 13.
Figure 15:
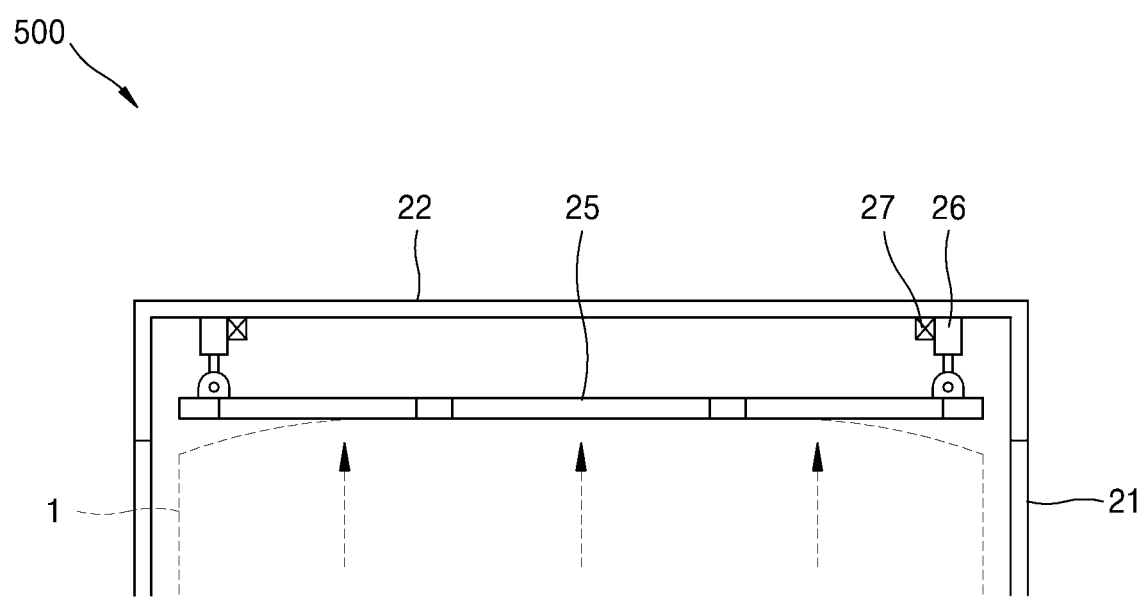
FIG. 15 is a cross-sectional view of a culture bag presser of the cell culture system of FIG. 13.

FIG. 13 is an exterior perspective view conceptually illustrating a cell culture system 500 according to still other embodiments of the present invention, FIG. 14 is an exploded perspective view of the cell culture system 500 of FIG. 13, and FIG. 15 is a cross-sectional view of a culture bag presser 25 of the cell culture system 500 of FIG. 13.

As illustrated in FIGS. 13 to 15, the movable plate 20 of the cell culture system 500 according to still other embodiments of the present invention may further include the culture bag presser 25 for pressing the culture bag 1 when the culture bag 1 accommodated in the accommodation space A inflates.

Herein, the culture bag presser 25 may include a window-shaped pressing frame consisting of horizontal and vertical bars. However, the culture bag presser 25 is not limited to the shape shown in FIG. 15 and may have various shapes, for example, a box shape shown in FIG. 8 or a modified window shape shown in FIG. 10.

Specifically, for example, as illustrated in FIG. 15, the movable plate 20 may further include a pressing actuator 26 mounted in the cover 22 to lift or lower the culture bag presser 25, and an inflation pressure gauge 27 for measuring an inflation pressure applied to the pressing frame.

Therefore, the controller 50 may, for example, suppress inflation of the culture bag 1 due to biological gases produced during cultivation, or operate a separate exhaust valve or exhaust pump, by applying an up/down control signal to the pressing actuator 26 based on an inflation pressure signal measured by the inflation pressure gauge 27.

According to the afore-described embodiments of the present invention, damage to cells included in a medium may be greatly reduced because no impeller or propeller is used, contamination of the medium due to the impeller or propeller may be prevented, a production cost of equipment may be greatly reduced, a degree of freedom and a degree of mixing of the medium may be increased because the medium may be mixed in multiple directions including forward, backward, leftward, rightward, upward, and downward directions, a semi-permanent lifespan may be achieved based on very stable operation through a plurality of cycles because a first actuator, a second actuator, and an auxiliary joint are precisely positioned at 120° with respect to a central joint, device scale, performance, efficiency, and productivity may be greatly increased by using a plurality of links, a cost and a production time may be greatly reduced, cells in the medium may be cultured while mixing the medium, and inflation of a culture bag due to biological gases may be suppressed or solved. However, the scope of the present invention is not limited to the above-described effects.

While the present invention has been particularly shown and described with reference to embodiments thereof, it will be understood by one of ordinary skill in the art that various changes in form and details may be made therein without departing from the scope of the present invention as defined by the following claims.

What is claimed is:

1. A cell culture system comprising:
   a body;
   a movable plate comprising an accommodation space accommodating a culture bag accommodating a medium to mix the medium, and being tiltable in multiple directions by a central joint mounted at a first location of the body;
   a first actuator mounted between the body and a second location of the movable plate to move the movable plate;
   a second actuator mounted between the body and a third location of the movable plate to move the movable plate;

an auxiliary joint mounted between the body and a fourth location of the movable plate to prevent vibration of the movable plate; and a controller for applying a control signal to the first and second actuators, wherein the body comprises:

a main frame for mounting the first actuator on a left side thereof, mounting the second actuator on a right side thereof, and mounting the central joint on a center thereof;

a case for protecting the main frame; and a plurality of caster wheels mounted under the main frame, wherein the body further comprises:

a wheel frame mounted between the caster wheels and the main frame; and a plurality of load cells mounted between the main frame and the wheel frame, wherein the plurality of load cells are mounted at locations corresponding to the caster wheels to obtain a load signal of loads applied toward a ground surface, and wherein the controller determines normal or abnormal operation by comparing a real-time load signal received from the load cells to a reference load signal received from the plurality of load cells and pre-stored when hydrodynamic flow characteristics of the medium is normal, and applies a control signal to the first and second actuators to follow a normal state, and wherein a first angle between a first reference line extending from the first location to the second location, and a second reference line extending from the first location to the third location is 120°, wherein a second angle between the second reference line and a third reference line extending from the first location to the fourth location is 120°, and wherein a third angle between the third reference line and the first reference line is 120°.

2. The cell culture system of claim 1, wherein each of the first and second actuators comprises:

a motor mounted on the body;

a first link rotated by the motor; and a second link having one end link-coupled to the first link, and another end link-coupled to the movable plate.

3. The cell culture system of claim 2, wherein the case comprises a link hole, through which the second link sufficiently passes, in a top surface thereof to accommodate at least a part of the first or second link.

4. The cell culture system of claim 1, wherein the central joint comprises a universal joint.

5. The cell culture system of claim 1, wherein the movable plate comprises:

a box-shaped medium tank having an opening thereon and comprising the accommodation space therein;

a cover for covering the opening of the medium tank;

a temperature controller mounted on a bottom surface of the medium tank to control a temperature of the medium; and a tank frame mounted under the bottom surface of the medium tank to support the medium tank.

6. The cell culture system of claim 5, wherein the movable plate further comprises a culture bag presser for pressing the culture bag when the culture bag accommodated in the accommodation space inflates.

7. The cell culture system of claim 6, wherein the culture bag presser comprises a pressing frame consisting of horizontal and vertical bars.

8. The cell culture system of claim 7, wherein the movable plate further comprises:

a pressing actuator mounted in the cover to lift or lower the culture bag presser; and an inflation pressure gauge for measuring an inflation pressure applied to the pressing frame, and wherein the controller applies an up/down control signal to the pressing actuator based on an inflation pressure signal measured by the inflation pressure gauge.

9. The cell culture system of claim 1, wherein the controller selects and applies at least one of a first actuator up-second actuator up control signal, a first actuator up-second actuator down control signal, a first actuator down-second actuator up control signal, and a first actuator down-second actuator down control signal to the first and second actuators to successively tilt the movable plate in forward, backward, leftward, and rightward directions.

10. The cell culture system of claim 9, wherein the controller applies a pause control signal to pause operation for a certain time and then restart the operation, while successively tilting the movable plate in forward, backward, leftward, and rightward directions.

11. The cell culture system of claim 9, wherein the controller applies a return control signal to return to a paused or horizontal state, when operation is restarted after being paused while successively tilting the movable plate in forward, backward, leftward, and rightward directions.

12. The cell culture system of claim 1, wherein the movable plate is tilted backward when both of the second and third locations are lifted by lifting both of the first and second actuators, or tilted forward when both of the second and third locations are lowered by lowering both of the first and second actuators.

13. The cell culture system of claim 1, wherein the movable plate is tilted rightward when the second location is lifted and the third location is lowered by lifting the first actuator and lowering the second actuator, or tilted leftward when the second location is lowered and the third location is lifted by lowering the first actuator and lifting the second actuator.

* * * * *